United States Patent [19]
Costales et al.

[11] Patent Number: 5,921,992
[45] Date of Patent: Jul. 13, 1999

[54] METHOD AND SYSTEM FOR FRAMELESS TOOL CALIBRATION

[75] Inventors: James B. Costales, Winchester; James S. Bath, Charlestown; Christophe P. Mauge, Melrose; Eric R. Cosman, Belmont, all of Mass.

[73] Assignee: Radionics, Inc., Burlington, Mass.

[21] Appl. No.: 08/840,198

[22] Filed: Apr. 11, 1997

[51] Int. Cl.[6] ................................................. A61B 19/00
[52] U.S. Cl. ................................................. 606/130; 601/1
[58] Field of Search ........................................ 606/130, 1

[56] References Cited

U.S. PATENT DOCUMENTS 5,483,961  1/1996  Kelly et al. ............................. 606/130

FOREIGN PATENT DOCUMENTS 9206645  4/1992  WIPO ................................... 606/130

*Primary Examiner*—Michael Buiz
*Assistant Examiner*—Julian W. Woo
*Attorney, Agent, or Firm*—Richard J. Birch; Hale & Dorr

[57] ABSTRACT

The intraoperative calibration of an arbitrary surgical instrument relative to a surgical navigation digitizing system is achieved by a calibration guide. The calibration guide is established in position and orientation relative to the digitizing system coordinate system. The surgical instrument is aligned to the calibration guide during calibration to establish its probe and end orientation in the digitizer coordinates. The instrument carries a marker structure which is trackable in the digitizer coordinates to enable tracking by rigid-body transformation of the instruments probe and end position after calibration in the calibration guide.

6 Claims, 2 Drawing Sheets

METHOD AND SYSTEM FOR FRAMELESS TOOL CALIBRATION

FIELD OF THE INVENTION

This invention relates generally to advances in medical systems and procedures for minimally invasive surgery. More particularly, this invention relates to an improved method and system for calibrating arbitrary surgical instruments with reference to surgical navigation equipment.

BACKGROUND OF THE INVENTION

In recent years, much progress in interactive surgical navigation has taken place. Use of mechanical, ultrasonic, and optical space digitizers for instruments in the operating room has increased. Use of several cameras to track surgical instruments and other objects in the operating field has been described in the papers by E. R. Cosman. Also, product literature from Radionics, Inc. of Burlington, Mass., carries some description. Commonly, two or more cameras are established to view the operating field. The cameras can be pre-calibrated to determine a reference coordinate system in the operating field in which infrared or optical objects can be tracked in three dimensions. It is common practice to attach LEDs or reflectors on instruments and quantitatively track them with the cameras. The LEDs may be placed in a known orientation relative to the tip and the direction of the instruments. Reference to the patient's anatomy is also made by placing LEDs or reflectors on the patient or on apparatus attached to the patient to follow and correct for patient movement. The instrument relative to the patient's anatomy can be referenced to graphics display of image scan data taken previously or during the surgery. This is done by a registration procedure. The paper by E. R. Cosman carries some description of this process.

Attachment of LED or reflector arrays on an arbitrary surgical instrument has been carried out, and the relationship of the tip of the instrument determined by touching a known point in the camera field and thus in the camera coordinate system.

However, an effective technique for calibrating the tip and direction of an arbitrary surgical probe, instrument, microscope, or other device in the operative field is desirable. A surgical instrument direction is an important quantity during surgery in addition to the tip position of the instrument, and a system and method to determine both the probe direction and the probe tip position is useful in clinical application.

SUMMARY OF THE INVENTION

The present invention is directed to a system and procedure for calibrating and/or determining the direction and/or tip position of a surgical device in an operative field which is being tracked. The use of a digital navigator to be used in this connection, together with a calibration guide, enables these surgical parameters to be known for an arbitrary instrument. The system and procedure of the present invention are different from any of the systems and procedures discussed in the background section. The advantages of the present system and method reside in their utility to make an arbitrary, unnavigated instrument into a quantitative, navigated instrument in both orientation and direction.

In one example, a camera tracking system views an operative field. An arbitrary instrument, such as forceps, endoscopes, or probes, is connected to an optical tracking arrangement consisting of an array or system of LEDs, reflectors, or other light markers that are tracked by the camera system. The instrument is connected to a calibration guide which has a fixture or alignment structure which has a known or a determinable orientation and position in the camera's optical field. The fixture accepts or guides the probe direction and probe tip position of the arbitrary surgical instrument. The known relationship of the optical tracking structure and the calibration guide fixture provides data to determine the direction and tip position of the surgical instrument in the three-dimensional coordinates of the camera tracking system. Now, by tracking the position of the light marker system, which is rigidly connected to the surgical instrument, the camera thereby tracks the probe and tip positions. The position of the instrument also can be determined relative to patients' anatomy and to data taken from an image scanner in image scan coordinates by registration of the camera coordinate system to the image scan data coordinates which is known (see, for example, the paper by E. R. Cosman).

In one example, the calibration guide is a holster or tube in which the instrument can be placed and docked. The tube and holster is in known relationship in the camera coordinate system to thereby determine the instrument direction and position relative to the camera system.

The present system and procedure has the advantages of enabling a general and unquantified instrument of arbitrary nature to be converted into a quantitative, navigable instrument whose position and direction can be tracked by the cameras. Prior to surgery, no pre-calibration of the instrument is necessary, according to the system and method of the present invention.

Another advantage of the present system and procedure is that it avoids need for pre-calibrated instruments for which direction and tip position must be known prior to surgery. Thereby, it opens up and wider range of existent instruments, some of which are very expensive and complex, to be interactively navigated in a tracking coordinate system.

These features and advantages, as well as others of the present method and system, will be apparent in the detailed description that follows.

BRIEF DESCRIPTION OF THE DRAWINGS

In the drawings, which constitute a part of the specification, embodiments exhibiting various forms and features hereof are set forth, specifically.

DESCRIPTION OF SOME PREFERRED EMBODIMENTS OF THE INVENTION

Figure 1:
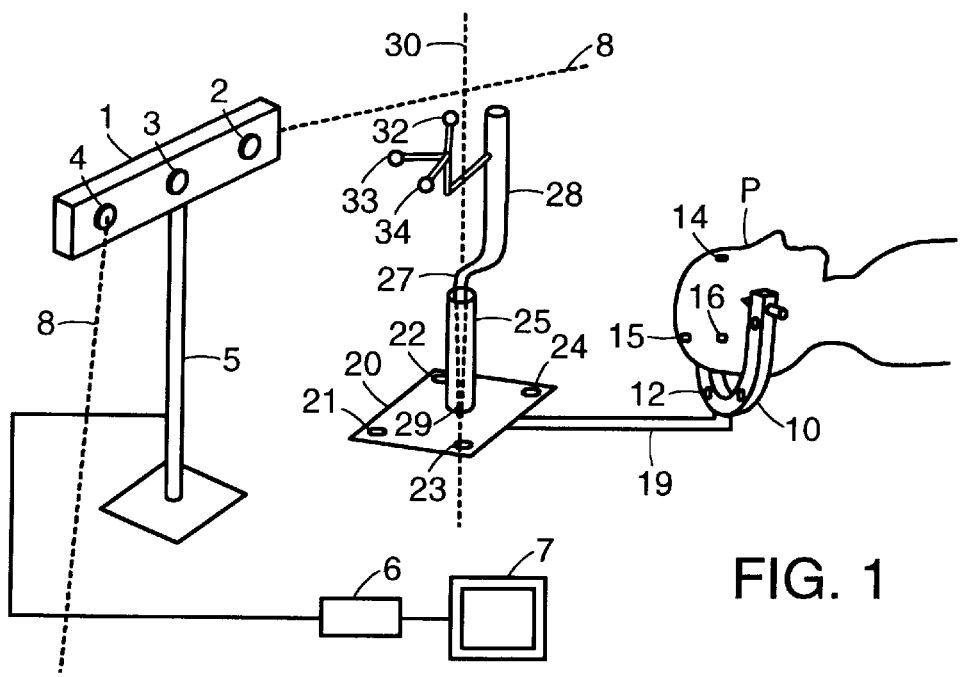
FIG. 1 is a schematic diagram of an operative setting showing the calibration guide and optical tracking device in accordance with the present invention.

Referring to FIG. 1, in accordance with the present method and system, a camera system 1 comprises cameras 2, 3, and 4 and is stably mounted on stand 5 fixed to the operating theater. There is a field-of-view or operative field of the cameras, indicated by dashed lines 8. Also, the camera system can have a camera coordinate system (not shown in FIG. 1) which references objects in the operative field to the cameras. The camera is connected to data processor 6 and display 7. This contains controls that can track a light-emitting or reflecting object in the field-of-view 8 and establish its coordinates relative to camera 1. Patient P is in the field-of-view and has light markers such as light emitters or reflectors 14, 15, and 16 placed on its anatomy. Alternatively, these could be natural landmarks which are used for calibration. Head clamp or immobilizer 10 also has light objects, such as element 12, which can be registered by camera 1. The use of such cameras and light markers is commonly known.

In accordance with the present invention, calibration guide 20 is affixed by element 9 relative to the patient. It has light markers 21, 22, 23, and 24, for example(the number of such markers may be variable), and a guide tube 25. The guide tube has a direction or axis indicated by dashed line 30, and an end point indicated by point 29 at the end of the guide tube 25. The guide tube is in a known position relative to the light markers. The light markers are determined or tracked by the camera system, so their position and orientation is known in the camera coordinate system. Thus the guide tube position is also known in the camera coordinate system. The probe end 27 of an instrument 28 is inserted or guided by the guide tube 25 so that the tip of the instrument is coincident with point 29. In this way, the instrument probe direction 27 is aligned with axis 30, and therefore known relative to the camera coordinate system 1. In addition, light marker elements 32, 33, and 34, or more are attached to the instrument 28, and also registered by the cameras 1. For example, if they are non-colinear, they will have a marker coordinate system associated with them which is also determined relative to the camera coordinate system. Thus, by rigid body transformation from the camera coordinate system, to the marker coordinate system, and to the probe guide, the orientation of the probe direction 27 can be calibrated relative to the cameras in the initial placement in the calibrated guide 25. Thereafter, any motion of the probe or instrument 28 in the field-of-view 8 enables the position of the probe end of the instrument 27 and its tip position to be determined in the camera coordinate system, by the above-mentioned rigid body transformation. Such transformations are used in the equipment of Radionics, Inc., for example, to track their dynamic reference frames and are commonly known in vector algebra.

In accordance with one embodiment, the guide tube 25 could have various fixturing or aligning structures to align the instrument probe direction, including variable diameter tubes, collet structures for closing down on the probe end 27, alignment rings at each end to visually align the probe end 27 as examples. The base of the structure 20 could have other varying shapes, and the light elements such as 21, 22, 23, and 24 could be reflectors or patterns of light markers, either discrete or continuous, so as to determine the direction and position of guide element 25. The guide tube 25 could be a chuck with a tube to close down on a probe such as 27 by a rotational movement.

As a specific example, the camera system could be similar to that produced by IGT Image-Guided Technologies, Boulder, Colo., and have three linear infrared CCD cameras 2, 3, and 4, or it could have two two-dimensional cameras, as the camera system of Northern Digital, Toronto, Canada. The light markers, such as 21, 22, 23, and 24 can be LEDs or reflective elements. Similarly, 32, 33, and 34 can be mounted on a rigid triad structure and be clamped to the handle of instrument 28, which for example may be a bipolar forceps, which are common in surgery. The data processor 6 and 7 could be similar to that used in the navigator products of Radionics, Inc., Burlington, Mass. The technique of light markers on head clamp 10 and on the patient could be similar to the dynamic reference frame used by Radionics, Inc., Burlington, Mass. The coupling between calibration guide 20 and the head clamp 10 could be as implemented by Radionics, Inc., Burlington, Mass.

Figure 2:
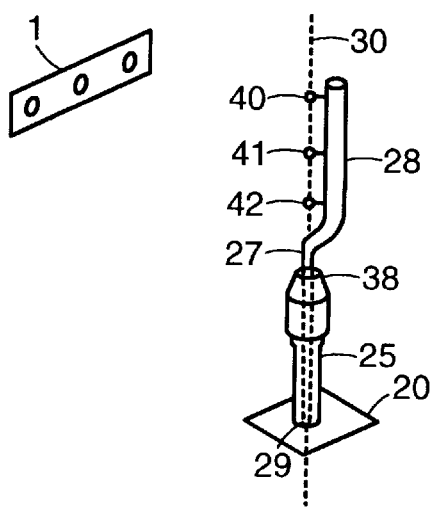
FIG. 2 illustrates the calibration of a passage calibration guide according to the present invention.

In accordance with other embodiments, FIG. 2 shows another calibration guide 20, which has a guide tube structure 25, and on its end a chuck 38, which can close down on a diameter of an instrument such as probe end 27 of instrument 28. Instrument 28 has a set of light markers 40, 41, and 42. There are three of these light markers shown, but there could be more and they could be in any type of arrangement. Camera system 1 is shown schematically and similar to that in FIG. 1. If the instrument 28 is an existing calibrated instrument so that its probe end and tip position 29 are already known in the coordinate system of cameras 1 by tracking of 40, 41, and 42, then inserting it into calibration guide 20 will determine the position of the calibration guide, both its axis direction 30 and its terminal end position.

In this way, in accordance with the present invention, an arbitrary calibration guide 20, without light markers attached to it (as shown in FIG. 1), can be calibrated at the time of surgery. This has the advantage that the calibration guide 20 can be a passive structure, and at the time of surgery its direction and position may be calibrated in the coordinate system of camera 1 during the operation.

Now, in accordance with the system and process of the present invention, an arbitrary instrument such as instrument 48 with probe end 47 can be placed into the calibration guide 20. The position of the calibration guide 20 and its axis 30 has been established, as described above in connection with FIG. 2. The chuck element 38 can be turned, as in the direction of the arrow 39, to close down around the axis 30 so as to clamp the probe end 47. The instrument 48 may be an arbitrary surgical instrument. At surgery, prior to its calibration, a clamp such as 50 can be attached to it, and an array 51 of light markers 52, 53, and 54 are attached and trackable by the cameras in the operative field. Array 51 can have a light marker coordinate system associated with it, so that tracking markers 52, 53, and 54 enable tracking of position and orientation of the marker coordinate system relative to the camera coordinate system. With the probe end 47 in the calibration guide tube 25, therefore the camera processor (as element 6 in FIG. 1) can register the orientation, length, and tip position of the instrument probe end 47.

Figure 3:
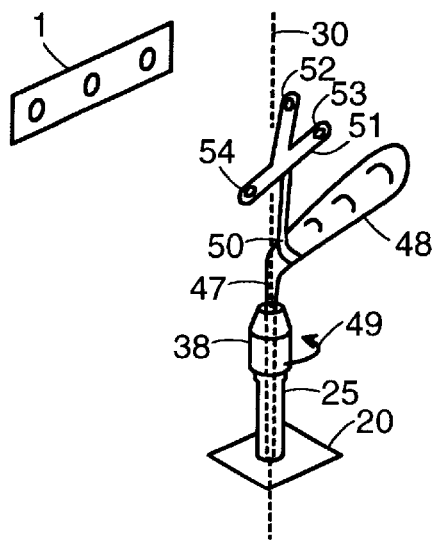
FIG. 3 illustrates the calibration of an arbitrary instrument with a tracking device in accordance with the present invention.

The embodiment of the system and process of the present invention shown in FIGS. 2 and 3 enables a passive calibration guide 20 to be calibrated by a known instrument 28, and thus to calibrate an unknown instrument 48 by means of attached light marker array 51. This has advantages to the surgeon, since his existent instruments 48 can thus be calibrated at the time of surgery both in direction and in tip position. No special pre-attachments of light marker arrays need be made, but the array can be attached to instrument 48 intraoperatively. During surgery, an instrument can be changed, and the process, as described above in association with FIG. 1 and FIG. 2 according to the present invention, can be implemented quickly. The calibration guide 20 can be sterilized, and the light arrays 51 can be arbitrary in form and geometry. Typically, non-colinear light arrays with three or more lights are useful to establish a rigid body light marker coordinate system with three dimensions associated with array structure 51. By rigid body transformations as described above, thereby the instrument probe end 27 can be established and tracked, both in direction and end position.

It should be recognized that a variety of configurations and designs of the calibration guide 25, the light array 51, the clamping mechanism 38, and the camera system are possible in accordance with the present system and method and desirable by those skilled in the art.

Figure 4:
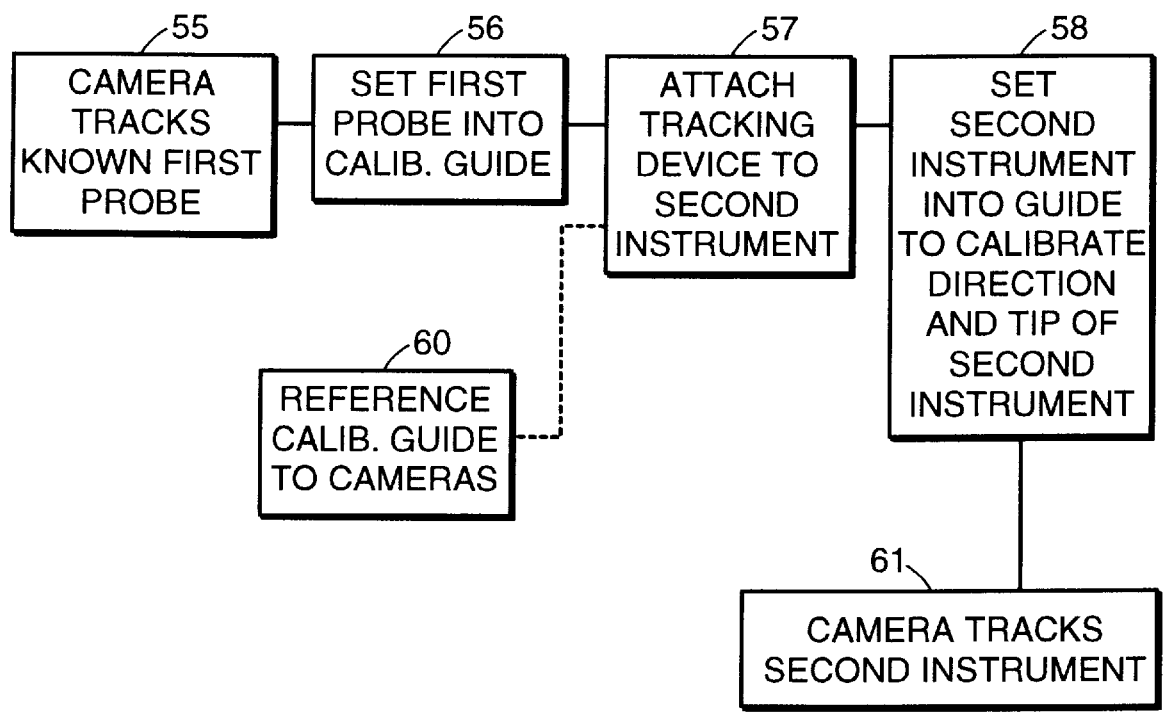
FIG. 4 illustrates a flow chart of the system and process in accordance with the present invention.

FIG. 4 shows a flow diagram for a process in accordance with the present invention. Element 55 illustrates the process step establishing a tracking camera system. In this step, it tracks a known probe, which may have light elements attached to it so that the position of the probe end and direction is known in the coordinate system of the camera. Element 56 represents the step of inserting or setting the first calibrated probe into a calibration guide. As described above, this establishes the orientation and position of the calibration guide relative to the camera coordinate system. Block 57 comprises the steps of attaching a light marker system that is detectable by the cameras to a second instrument. The second instrument may be an arbitrary instrument with a distal end and a probe direction which the surgeon desires to calibrate and track in the coordinates of the camera. Once the light marker array is attached to the second arbitrary instrument, the second instrument is set into the calibration guide, as illustrated by block 58. The calibration guide having been calibrated, represented by block 56, now provides a direction and position associated with the second instrument. This enables, by the processor (as element 6 of FIG. 1) or the camera system, establishment of the orientation and position (its probe direction and probe end) of the second instrument, as described above.

When the second instrument is now removed from the calibration guide, the light marker array attached in step 57 establishes the orientation and position thereafter of the second instrument as it is moved or repositioned in the operative field of the cameras.

As an alternative initial step in the process of FIG. 4, in accordance with the present invention, the calibration guide structure may be established relative to the camera coordinates by an alternative process. For example, as in the illustration of FIG. 1, guide may have light markers of known orientation relative to its position and guide tube direction. If this has been established beforehand and is tracked by the camera system, then this step can be a predicate to steps 57 and 58. It then represents a pre-calibrated calibration guide for the purpose of calibrating the direction and position of the second instrument, as described in connection with block 57.

In accordance with the present invention, variations of the calibration guide 20 are possible by those skilled in the art. It may comprise a holster, guide tube, orifice, series of coaxial rings, clamp structures, alignment ruler, series of straight edges or marker points to establish an axis end point position, or other structures adapted to guide and calibrate an instrument probe and end position.

Light marker array 51 may take various forms in accordance with the present invention. It can be a lightweight triangle made of metal or plastic which can be clamped, as in FIG. 3, with a lightweight C-clamp 50 to the handle or shank of an arbitrary instrument 48. The instrument may be a forceps, drill guide, auger, surgical drill, endoscope, cannula system for biopsy or aspiration, and other various instruments commonly used in the operating theater. The light array can be a pattern of reflectors or one large reflector of a given shape or a pattern of linear lines of emitted light or reflected light, recognizable by the camera tracker (as element 1 in FIG. 1) and data processor (as element 6 in FIG. 1).

It should be recognized that various digitizers or tracking systems, devices, and techniques could be used in accordance with the present invention. For example, instead of a camera system and light markers, an ultrasonic detector with sonic markers or radiofrequency detector with associated markers could be used.

In view of these considerations, as would be apparent by persons skilled in the art, implementations and systems should be considered broadly and with reference to the claims set forth below.

What is claimed is:

1. A system for calibrating the position and direction of a surgical instrument in the coordinate system of a camera system that tracks the surgical instrument in an operative field comprising:

a. a camera system, having a camera coordinate system, adapted to track objects in the operative field having light markers attached to them;

b. a surgical instrument having a probe direction and a probe end;

c. a light marker system having a light marker coordinate system, the light marker system being adapted to attach to the surgical instrument and can be tracked by the camera system to determine the light marker coordinate system relative to the camera coordinate system;

d. a calibration guide that is adapted to align the probe direction and probe end in a known position relative to said camera coordinate system;

whereby after alignment of said probe direction and probe end in the calibration guide, said probe direction and said probe end can be tracked by said camera system relative to said camera coordinate system.

2. The system of claim 1 wherein said calibration guide comprises a fixturing system for said surgical instrument and a calibration light marker system that is tracked by said camera system which is in a known orientation to said fixturing system.

3. The system of claim 1 wherein said calibration guide comprises a fixturing system for said surgical instrument, and a calibrated probe having a known probe direction and known probe tip that are tracked by said camera system in said camera coordinate system, so that when said known probe is aligned in said fixturing system, then the orientation and position of said fixturing system is determinable in said camera coordinate system.

4. A process for interoperative instrument calibraton for use with a camera system adapted to track surgical instruments comprising the steps of:

a. placing a camera system to view an operative field, the camera system having a camera coordinate system, and said camera system being adapted to detect the position of light elements within the operative field to provide data representation of the position of the light objects in the camera coordinate system;

b. attaching a light marker system to a surgical instrument, the light marker system having a marker coordinate system, so that when said light marker system is tracked by said camera system the marker coordinate system is determined relative to said camera coordinate system, and the surgical instrument having a probe direction and a probe tip;

c. establishing a calibration guide within said surgical field having a fixture to align the probe direction and the probe tip in a determined position relative to said camera coordinate system while determining said marker coordinate system position in said camera coordinate system, thereby to establish the interoperative calibration of said probe direction and said probe tip in said camera coordinate for different positions of said surgical instrument by tracking said marker coordinate system;

d. tracking said probe direction and said probe tip of said surgical instrument within said operative field by tracking said marker coordinate system by said camera system.

5. A system for calibrating the position and direction of a surgical instrument in the coordinate system of a digitizing tracker that tracks the surgical instrument in an operative field comprising:

a. a digitizing tracker, having a tracker coordinate system, adapted to track objects in the operative field having tracking light markers attached to them;

b. a surgical instrument having a probe direction and a probe end;

c. a tracking marker system having a marker coordinate system, said tracking marker system being adapted to attach to the surgical instrument and can be tracked by the digitizing tracker to determine the marker coordinate system relative to the tracker coordinate system;

d. a calibration guide that is adapted to align the probe direction and probe end in a known position relative to said tracker coordinate system;

whereby after alignment of said probe direction and probe end in the calibration guide, said probe direction and said probe end can be tracked by said digitizing tracker relative to said tracker coordinate system.

6. A process for interoperative instrument calibraton for use with a digitizing tracker adapted to track surgical instruments comprising the steps of:

a. placing a digitizing tracker to view an operative field, the digitizing tracker having a tracker coordinate system, and detecting the position of light elements within the operative field to provide data representation of the position of the light elements in the tracker coordinate system;

b. attaching a tracking marker system to a surgical instrument, the tracking marker system having a marker coordinate system and being tracked by said digitizing tracker to determine a marker coordinate system relative to said tracker coordinate system, and the surgical instrument having a probe direction and a probe tip;

c. establishing a calibration guide within said surgical field having a fixture to align the probe direction and the probe tip in a determined position relative to said tracker coordinate system while determining said marker coordinate system position in said tracker coordinate system, thereby to establish the interoperative calibration of said probe direction and said probe tip in said tracker coordinate for different position of said surgical instrument by tracking said marker coordinate system;

d. tracking said probe direction and said probe tip of said surgical instrument within said operative field by tracking said marker coordinate system by said digitizing tracker.

* * * * *